United States Patent
Sullivan et al.

(10) Patent No.: US 11,010,374 B2
(45) Date of Patent: May 18, 2021

(54) METHOD AND SYSTEM FOR BUILDING A DATA GROUPING PLATFORM

(71) Applicant: International Business Machines Corporation, Armonk, NY (US)

(72) Inventors: Stephanie L. Sullivan, Belleville, MI (US); Susan L. Silagi, Ann Arbor, MI (US); Anne E. Fischer, Chelsea, MI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 344 days.

(21) Appl. No.: 15/851,076

(22) Filed: Dec. 21, 2017

(65) Prior Publication Data
US 2019/0197155 A1 Jun. 27, 2019

(51) Int. Cl.
| | | |
|---|---|---|
| *G06F 16/30* | (2019.01) | |
| *G16H 10/60* | (2018.01) | |
| *G06F 16/242* | (2019.01) | |
| *G06F 16/2457* | (2019.01) | |
| *G06F 16/2455* | (2019.01) | |
| *G16H 40/20* | (2018.01) | |

(52) U.S. Cl.
CPC ........ *G06F 16/244* (2019.01); *G06F 16/2457* (2019.01); *G06F 16/24565* (2019.01); *G16H 10/60* (2018.01); *G16H 40/20* (2018.01)

(58) Field of Classification Search
CPC .. G16H 10/60; G16H 40/20; G06F 16/24565; G06F 16/2457; G06F 16/244
USPC .................................................... 707/737
See application file for complete search history.

(56) References Cited

U.S. PATENT DOCUMENTS

| | | | | |
|---|---|---|---|---|
| 8,069,080 | B2* | 11/2011 | Rastogi | G06Q 30/0202 |
| | | | | 705/7.41 |
| 8,260,635 | B2* | 9/2012 | Hasan | G06Q 50/24 |
| | | | | 705/2 |
| 9,613,068 | B2 | 4/2017 | Tsirogiannis et al. | |
| 9,779,129 | B1* | 10/2017 | Lequeux | G06F 16/24 |
| 2005/0289524 | A1 | 12/2005 | McGinnes | |
| 2009/0070103 | A1* | 3/2009 | Beggelman | G06F 40/20 |
| | | | | 704/9 |
| 2010/0325170 | A1 | 12/2010 | Bloesch et al. | |
| 2011/0191343 | A1 | 8/2011 | Heaton et al. | |
| 2011/0246231 | A1* | 10/2011 | Sie | G06Q 50/22 |
| | | | | 705/3 |
| 2014/0350954 | A1 | 11/2014 | Ellis et al. | |
| 2014/0372147 | A1* | 12/2014 | White | G06F 16/2455 |
| | | | | 705/3 |

(Continued)

*Primary Examiner* — Kuen S Lu
(74) *Attorney, Agent, or Firm* — Michael Best & Friedrich LLP

(57) ABSTRACT

A method and system for creating a data grouping platform for grouping data from disparate locations and sources, according to a user-defined aggregate. The method and system includes a method for receiving a user-defined aggregate, a user-defined trigger event, and a plurality of user-defined grouping criteria and parameters for creating the user-defined aggregate. The system and method also allows for a user to identify input data sets and sources for creating the grouped aggregates. Once the method and system receives the user-defined parameters, the method and system builds a platform to group data and build data aggregates based on the user-defined criteria.

20 Claims, 7 Drawing Sheets

(56) References Cited

U.S. PATENT DOCUMENTS

2016/0103897 A1* 4/2016 Nysewander ....... G06F 16/2428
707/602
2016/0321410 A1* 11/2016 Timmerman ......... G06F 19/326
2017/0185723 A1* 6/2017 McCallum ............ G06F 19/328

* cited by examiner

METHOD AND SYSTEM FOR BUILDING A DATA GROUPING PLATFORM

BACKGROUND

The present disclosure relates to methods and systems for building a technology platform for grouping disparate data sets for applied analysis.

Data grouping, generally, relates to the process of combining data around a common unit of analysis. In some cases, the data is contained in multiple disparate and distributed data sources, and the process of grouping particular sets of data includes new and novel approaches for aggregating and combining the data to summarize it in a coherent manner and for applied analysis. In the healthcare context, for example, there may be multiple data sets coming from multiple sources, all of which are related to a single encounter with the healthcare system. For example, for an outpatient surgery, there may be data from an anesthesia claim, data from a surgical claim, data for a nursing claim, data for a facility claim, data for a pharmaceutical claim, and various other data sets related to the outpatient surgery event. In order to understand more about the outpatient surgery, an aggregate may be created to group all data that is related to the outpatient surgery, but is contained in the multiple disparate data sets. Thus, an aggregate may facilitate a way to summarize or relate the otherwise distributed information so that an informed analysis may be derived from the otherwise disparate data. By creating the aggregate, multiple similar events may be analyzed, compared, and/or used as a basis for making institutional decisions to positively impact business and monetary efficiencies. The process of grouping disparate sets of data around an aggregate, however, requires diverse and complicated logic rules for assimilating the data, and is typically accomplished by a hard-coded process, providing limited built-in flexibility.

SUMMARY

According to a first aspect, the disclosure provides a method for building a data grouping platform. The data grouping platform groups data from a plurality of data sets around a user-defined aggregate. Specifically, the method comprises receiving at a processor, a format for the user-defined aggregate and a user-defined trigger. The user-defined trigger forms a basis for grouping data from the plurality of data sets around the user-defined aggregate. The method also comprises receiving at a processor, criteria for grouping data from the plurality of data sets into the user-defined aggregate. The method further comprises creating and storing in a computer readable, non-transient storage medium, a process to identify a first set of data in the plurality of data sets based on the user-defined trigger, review the first set of data from the plurality of data sets based on the criteria for grouping data from the plurality of data sets to identify a second set of data, and build at least one aggregate comprising the second set of data, based on the format for the user-defined aggregate.

According to another aspect, the disclosure provides a system for building a data grouping platform around a user-defined aggregate. The system comprises a user interface for inputting the user-defined aggregate, a user-defined trigger, and criteria for grouping data from a plurality of data sets. The system also includes a data processing engine configured to receive a format for the user-defined aggregate and receive the user-defined trigger, wherein the user-defined trigger forms a basis for grouping data from a plurality of data sets around the user-defined aggregate. The data processing engine is also configured to receive the criteria for grouping data from the plurality of data sets into the user-defined aggregate. Further the data processing engine is configured to create and store, in a computer readable, non-transient storage medium, a process to identify a first set of data from the plurality of data sets based on the user-defined trigger, to review the first set of data from the plurality of data sets based on the criteria for grouping data from the plurality of data sets to identify a second set of data, and build at least one aggregate comprising the second set of data, based on the format for the user-defined aggregate.

In yet another aspect, the disclosure provides a computer program product for building a data grouping platform. The computer program product comprises a computer readable, non-transient storage medium having program instructions that are executable by a data processing engine to receive a format for the user-defined aggregate and receive a user-defined trigger. The user-defined trigger forms a basis for grouping data from the plurality of data sets around the user-defined aggregate. The program instructions also cause the data processing engine to receive a plurality of criteria for grouping data from the plurality of data sets into the user-defined aggregate. Further, the program instructions cause the data processing engine to create and store in a computer readable, non-transient storage medium, a process to identify a first set of data in the plurality of data sets based on the user-defined trigger, review the first set of data from the plurality of data sets based on a first criteria of the plurality of criteria for grouping data from the plurality of data sets, to identify a second set of data, and to review the second set of data based on a validation criteria of the plurality of criteria for grouping data from the plurality of data sets, to identify a validated set of data. Finally, the program instructions also cause the data processing engine to, build at least one aggregate comprising the validated set of data, based on the format for the user-defined aggregate.

These and other aspects, objects, and features of the present disclosure will be understood and appreciated by those skilled in the art upon studying the following specification, claims, and appended drawings.

DETAILED DESCRIPTION

The present disclosure provides a method and system for building a data grouping platform around a user-defined aggregate. According to aspects described herein, the method and system may include receiving user-defined parameters for building an aggregate, such as relevant input data sources or other data files, receiving a trigger event for the aggregate, and receiving various rules and criteria for grouping data around the trigger event. Thereafter, the method and system provides a mechanism to consider the user-defined inputs and build a platform that can ultimately build the user-defined aggregate. For purposes of the present disclosure, an "aggregate" may be defined as a new data entity, unit of analysis, or other data grouping that is created from a plurality of disparate data sources. Further, a "trigger event" may be defined as a starting point for creating an aggregate.

In some cases, an aggregate may be created to summarize disparate, yet related data records. For example, an aggregate could summarize disparate medical claims records that describe a single healthcare event. In other cases, an aggregate may be built to analyze multiple aggregates that have been previously formed, such as aggregates to analyze healthcare activity in various geographic regions. Accordingly, aggregates may be centered around any type of data, entity or organization where it is desired to group and explain disparate data sets. For example, in the healthcare field, aggregates may be centered around patients, hospitals, providers, pharmaceutical providers, and the like. However, aggregates may also be built in other environments or industries unrelated to healthcare, and it will be understood that the present disclosure is not limited in the scope of its application to any specific industry, environment, or type of data.

Figure 1:
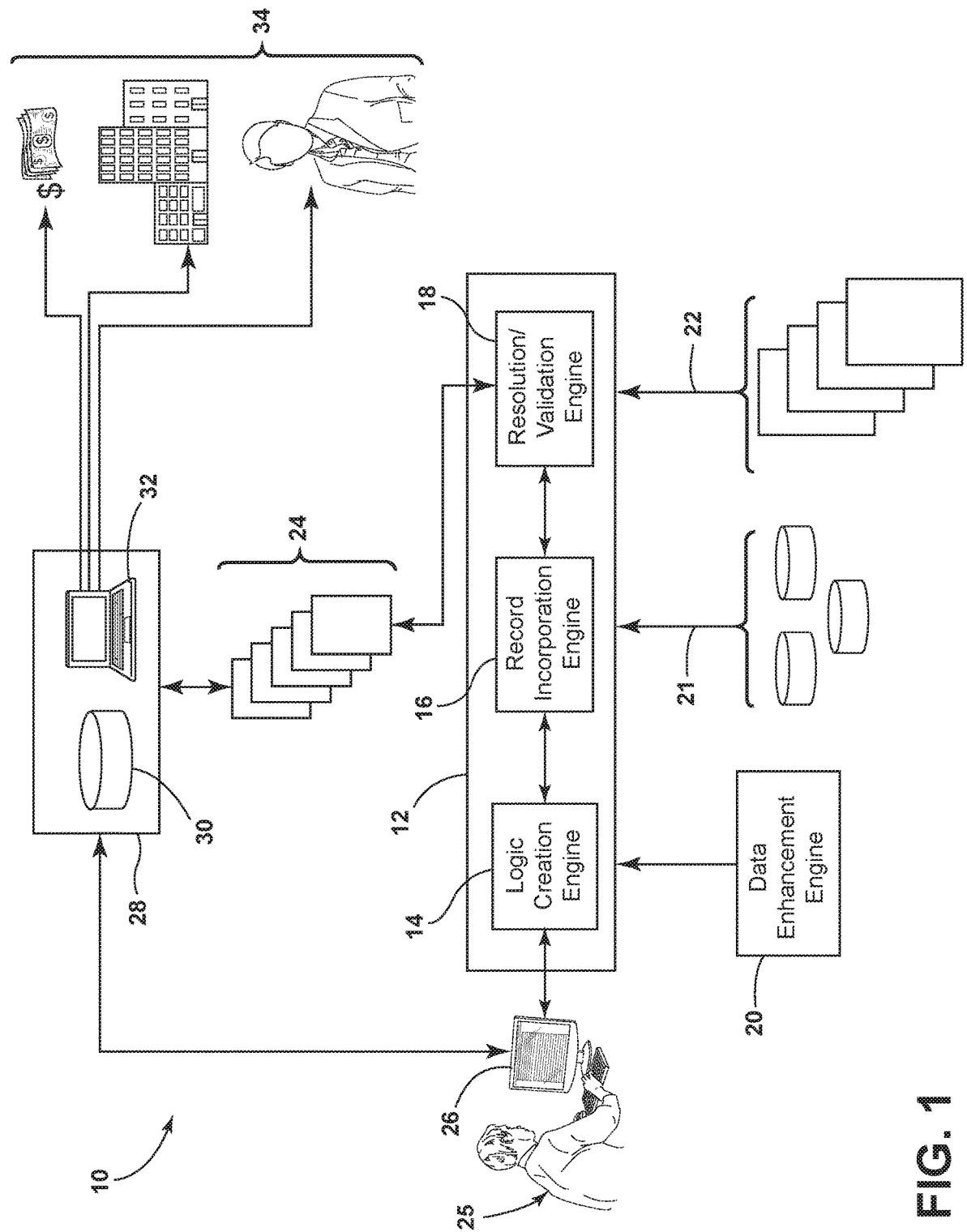
FIG. 1 depicts a schematic representation of a system for building a data grouping platform, according to an embodiment of the present disclosure.

FIG. 1 depicts a schematic representation of a system 10 having components on which embodiments of the present disclosure may be implemented. In accordance with an embodiment described herein, a system 10 includes a data processing engine 12, which can include a platform, such as one or more sub-engines, for creating the user-defined data aggregate 24. In some cases, the data aggregates may be created and used by one or more organizations 28, e.g., a healthcare system, business, government, non-profit organization, or other organized entity. Data processing engine 12 may also be coupled to one or more user input devices 26 for receiving data grouping instructions, as well as one or more data sources, such as one or more databases 21, data input files 22 or other sources of input data.

In at least one case, data processing engine 12 may be configured to receive information from a user 25 to create a user-defined data aggregate 24. Accordingly, data processing engine 12 may include one or more functional sub-engines for separately receiving information about a user-defined aggregate and trigger event, receiving the logic or criteria for creating the user-defined aggregate, reviewing data to determine whether data records should be incorporated into an aggregate, and mechanisms to review and validate the aggregate that is created. In some cases, the sub-engines may include, but are not limited to, logic creation engine 14, data record incorporation engine 16, and aggregate resolution and validation engine 18. However, in other cases, other types of processing sub-engines may be incorporated within system 10.

Logic creation engine 14 may be configured to apply one or more rules to data inputs, as described in more detail below, for example in relation to FIGS. 4-6 in accordance with an embodiment of the disclosure. In some embodiments, logic creation engine 14 may also be coupled to various other data enhancement engines 20. For example, in a healthcare context, data enhancement engine 20 may include an engine to map one or more data sets to describe a disease stage or one or more comorbidities related to a patient or to medical data. Record incorporation engine 16 and resolution and validation engine 18 may be configured to apply the data grouping logic created by logic creation engine 14, as described in more detail below with relation to FIGS. 5-6, in accordance with an embodiment of the disclosure. Accordingly, data processing engine 12 may be configured to produce one or more processes, outputs, or the like for an organization 28, or other entity, to create user-defined data grouping processes.

As described in more detail below, data processing engine 12 may also include, or be coupled with, one or more data enhancement engines 20, databases 21, data input files 22, or other data records or data repositories that store information such as input data libraries, input variables, and algorithms for implementing data grouping logic. Data processing engine 12 may also include one or more servers including any processor, server (including a cloud server), mainframe computer, or other processor-based device capable of facilitating communication and running software programs or other applications.

With reference to FIG. 1, the illustrated embodiment depicts data processing engine 12 as being broken up into a plurality of functional sub-engines, including logic creation engine 14, record incorporation engine 16, and resolution and validation engine 18. However, it should be understood that all data processing engine functions may be achieved in more or fewer sub-engines, such that any number of data processing engines may be programmed, configured, or connected to receive and transmit the same information or commands, and perform the same functionality as described with respect to the various sub-engines depicted in the illustrated embodiment. For example, where there are descriptions regarding the respective separate functionalities of logic creation engine 14, record incorporation engine 16, and resolution and validation engine 18, such functionality may also be carried out by a single data processing device. In other words, in an embodiment that includes a logic creation engine 14, record incorporation engine 16, and resolution and validation engine 18, these sub-engines can be included within the same hardware component (and at the same geographic location) or in different hardware components (and at different geographic locations), and still fall within the spirit and scope of the present disclosure. As shown in FIG. 1, data enhancement engine 20 may also be included in the same hardware as data processing engine 12, or may be communicatively connected in separate hardware. Input data may also be stored in one or more data stores or databases, including data store 30. Data store 30 may be connected to data processing engine 12. In operation, one or more management devices 34 physically located in, or otherwise communicatively connected to, organization 28, as well as input device 26, may access the one or more data aggregates 24 created by data grouping system 10. In at least some embodiments, aspects of the present disclosure may allow organization 28 to develop ways to easily group and analyze large disparate amounts of data to implement improvements and efficiencies to organization operations, collectively 34.

Figure 2:
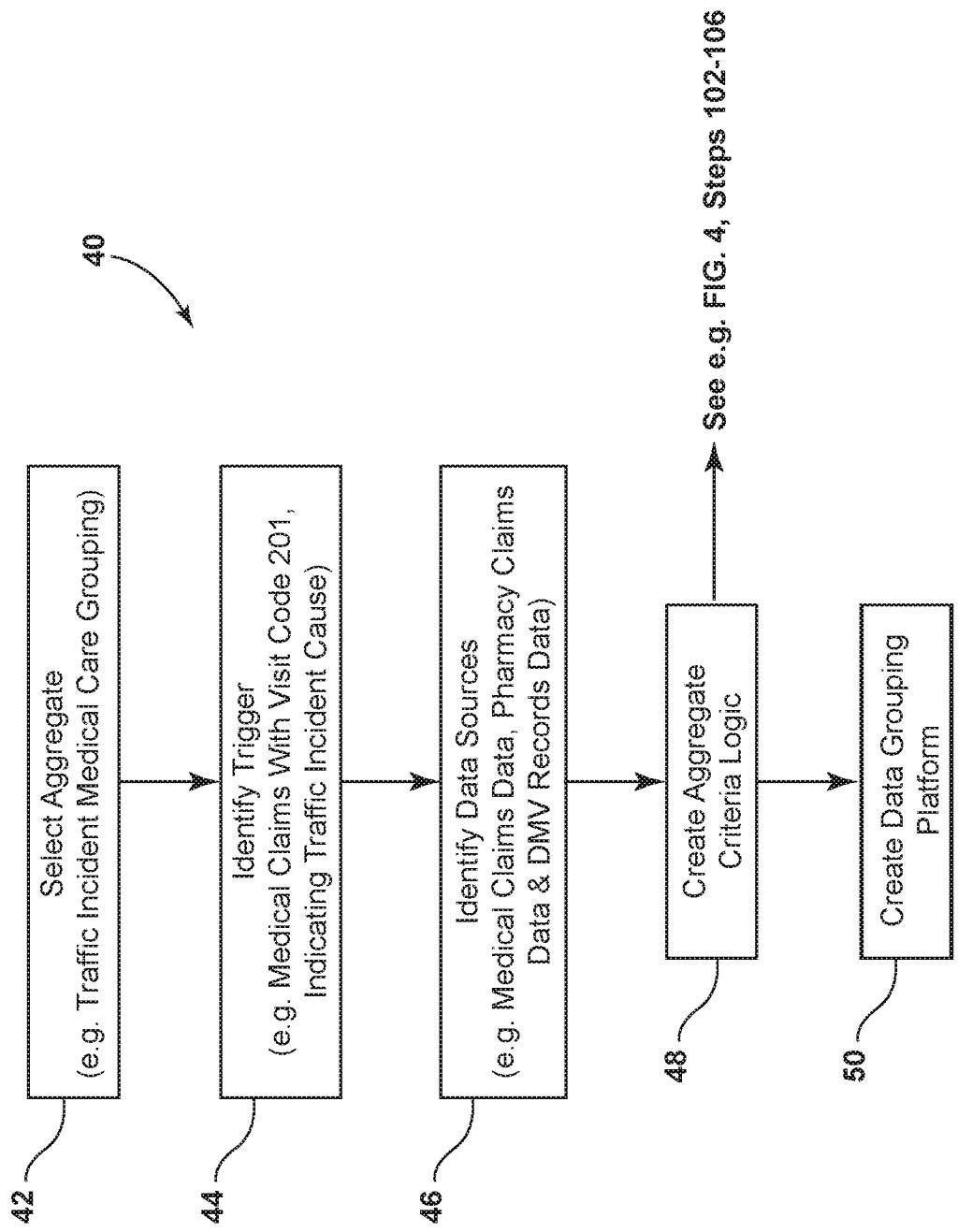
FIG. 2 depicts a flowchart of a method for building a data grouping platform, according to an embodiment of the present disclosure.

FIG. 2 depicts a flowchart 40 of an embodiment of an overall method for building a data grouping platform as may be implemented by data processing engine 12, described herein. At a high level, a data grouping platform allows a user or other entity to identify a data aggregate around which it is desired to collect, organize, and explain information or data from multiple and disparate data sources. Accordingly, the general process may include selecting an aggregate (step 42); identifying a trigger or trigger event for creating the aggregate (step 44); identifying the data sources to be used in creating the aggregate (step 46); identifying criteria for grouping data from the data sources for creation of the aggregate (step 48); and creating the data grouping platform to then build the aggregate that is selected (step 50).

The general process set forth in the flowchart of FIG. 2 is generic in that the process may be applied across many different types of data scenarios, for example, in the healthcare field, in government data tracking scenarios, academic settings, and any other setting where it may be desirable to collect and understand data from a plurality of data sources. For purposes of explanation, however, the methods and system described herein are explained in the context of creating a simplified and exemplary data grouping platform around understanding medical care and medical care-related expenses stemming from traffic incidents, such as automobile accidents. It will be understood, however, that any specific examples provided herein, including the exemplary traffic incident medical care data grouping platform example, are only exemplary and comprise examples of many embodiments that are contemplated in conjunction with the methods and systems described herein.

Figure 3:
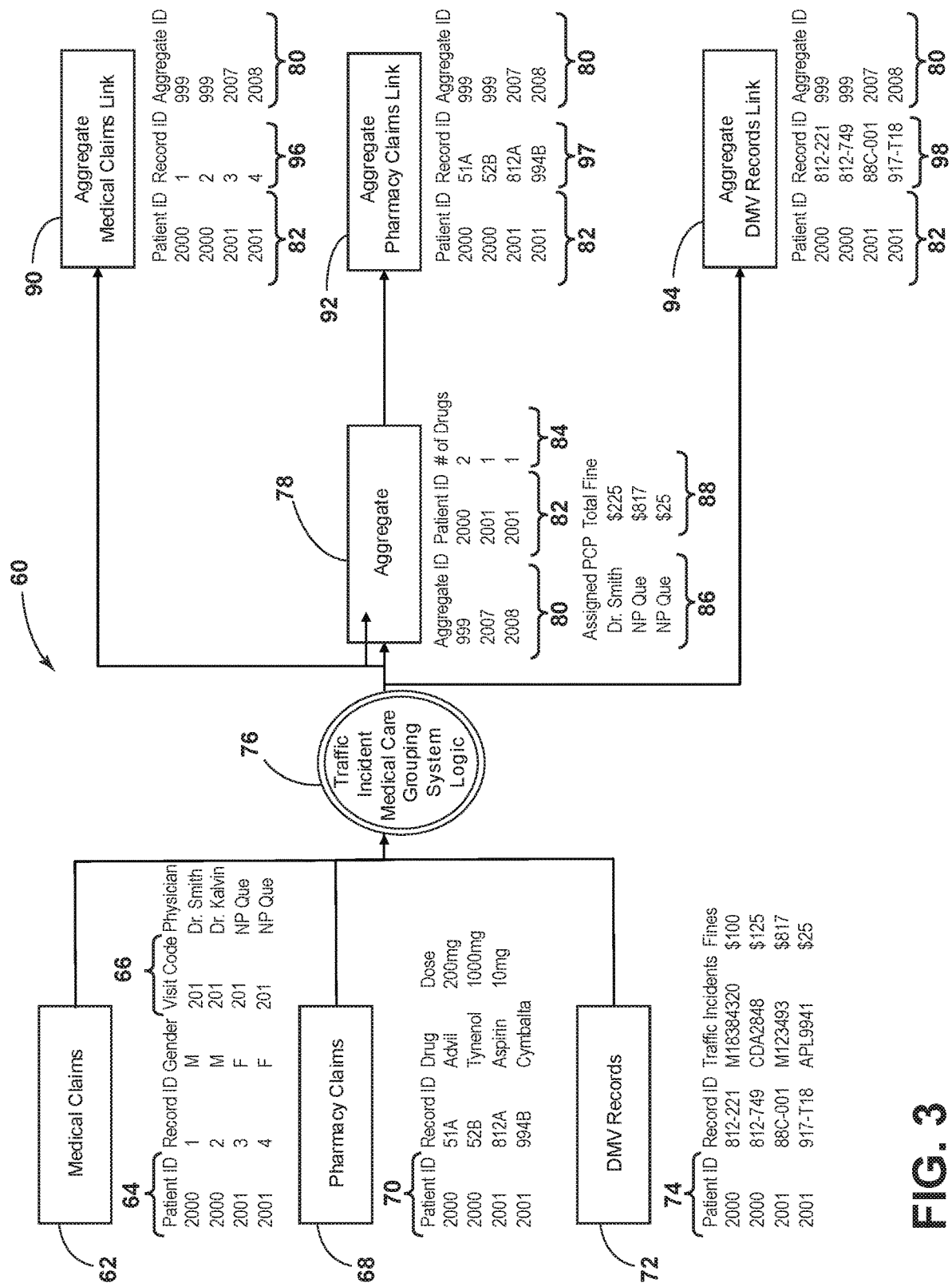
FIG. 3 depicts various inputs and outputs of a data grouping platform, according to an embodiment of the present disclosure.

FIG. 3 depicts exemplary components of a traffic incident medical care grouping system 60, according to the illustrated embodiment. In particular, according to methods described herein, a user might create a traffic incident medical care grouping system logic 76 to create a plurality of data traffic incident medical care aggregates 78, ultimately summarizing and describing medical data related to traffic incidents. In some cases, traffic incident medical care grouping system 60 may group data from multiple disparate data sources, including but not limited to, medical record data sources and Department of Motor Vehicle (DMV) data sources. Thus, aligning the example with the method described in flowchart 40, a user may identify a traffic incident medical care aggregate 78 as a basis for collecting and summarizing information at step 42. From there, at step 44 of flowchart 40, the user may create a trigger event for grouping the traffic incident data. For example, referring to FIG. 3, a user may identify a traffic incident medical care aggregate trigger 66, which may include identifying all medical claims having a visit code "201." According to the illustrated embodiment, visit code "201" identifies a particular medical event as being related to a traffic incident. However, in the illustrated example, the trigger could also be defined in other ways as would be contemplated by a skilled artisan, such as identifying DMV records where an emergency vehicle, such as an ambulance, delivered a vehicle occupant to a healthcare facility.

Moving on to step 46 of FIG. 2, in order to create the traffic incident medical care grouping system logic 76 of the illustrated example, a user may identify multiple data sources for input into traffic incident medical care grouping system 60, and for review according to a specified set of criteria or logic, i.e., traffic incident medical care grouping system logic 76. As shown in FIG. 3, according to the illustrated embodiment, the data sources may include medical claims data source 62, pharmacy claims data source 68, and DMV records data source 72. Of course it will be understood that many more data sources or input libraries, as described in more detail below, could be identified or used as data input, and that the illustrated example is simplified for the purpose of description herein. Further, as shown in FIG. 3, each of medical claims data source 62, pharmacy claims data source 68, and DMV records data source 72 may include a linking field which can serve to link related records across the plurality of data sources. Specifically, medical claim patient ID field 64, pharmacy claim patient ID field 70, and DMV records patient ID field 74 each identify a particular patient or driver which can serve to link information across data sources. Accordingly, the logic for the data grouping platform may identify, or create, at least one field that can provide a link across disparate data sources. In the embodiment of FIG. 3, the linking field includes a patient ID field, however, in other cases it may include a time window such as a begin date to an end date, a specific location such as a specific DMV office, or other linking attribute as may be contemplated by a person skilled in the art.

Moving forward to step 48 of flowchart 40 in FIG. 2, a user may next identify criteria or logic that instructs the data grouping platform on how to incorporate various pieces of data from the plurality of data sets and various data sources to build the aggregate. This may include defining logic that determines whether or not a specific data record is brought into the aggregate, excluded from the aggregate, or should form the basis of a new aggregate and would be an input to logic creating engine 14. In some cases, this may include matching a field within a data source, such as the patient ID field described above with respect to the illustrated embodiment of FIG. 3. In other cases, however, other logic and other criteria may be used, including multiple iterations of logic. For example, in some embodiments, the criteria may consider whether the data falls within a specific time window. In other embodiments, the logic may be based on a combination of a field match and a time window. In still other embodiments, the logic may specify comparison of a trigger event or data field to another data record already identified in the aggregate, or reviewing components of an aggregate that has already been identified or built to other criteria. Accordingly, it should be understood that the criteria for grouping the data may be identified by the user and include many different kinds of logic as would be understood by the skilled artisan. The process of identifying and implementing the data grouping logic is further described with relation to FIGS. 4 and 5.

Step 50 of flowchart 40, creating the data grouping platform, by data processing engine 12, includes building the computer-implemented process to perform the data groupings, and to build the aggregate and related outputs. As related to the illustrated embodiment example in FIG. 3, this may include creating traffic incident medical care grouping system logic 76, creating traffic incident medical care aggregate 78, and creating additional cross-reference outputs (aggregate medical claims link table 90, aggregate pharmacy claims link table 92, aggregate DVM records link table 94).

In the example of FIG. 3, traffic incident medical care aggregate 78 includes a plurality of aggregate fields, including but not limited to, an aggregate ID field 80 for identifying the aggregate record and linking it to other cross-reference records; the aggregate patient ID field 82; an aggregate number of drugs field 84; an aggregate primary care physician (PCP) field 86; and an aggregate total fine field 88. The traffic incident medical care grouping system logic 76 may also create cross-reference files to describe specific aspects of the traffic incident medical care aggregate 78 and to link back to the overall traffic incident medical care aggregate 78. According to the illustrated embodiment, the cross-reference files may include an aggregate medical claims link table 90, an aggregate pharmacy claims link table 92, and an aggregate DMV records link table 94. The aggregate cross-reference tables may further include a linking field such as aggregate ID field 80 linking back to traffic incident medical care aggregate 78.

Figure 4:
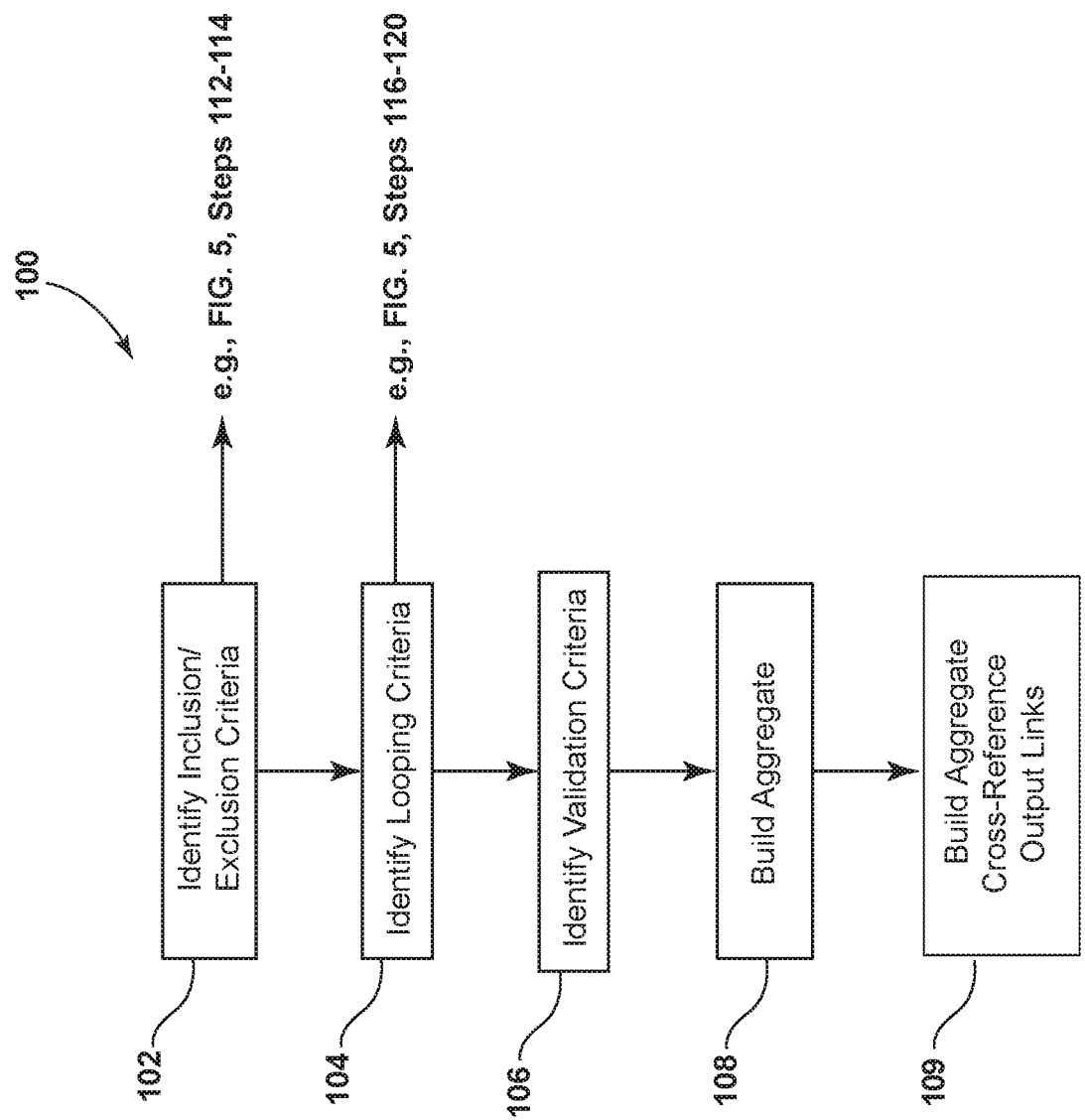
FIG. 4 depicts another flowchart of a method related to building a data grouping platform, according to an embodiment of the present disclosure.

FIG. 4 depicts a flowchart 100 further describing portions of a method and system for creating a data grouping platform. In particular, flowchart 100 describes steps that may take place in the various sub-engines of data processing engine 12 after a user identifies an aggregate and an aggregate trigger event, according to an embodiment. Generally, the method may include the identification of logic or criteria to identify one or more data sets for the aggregate as well as actual creation of the data aggregate and the aggregate cross-reference data. Thus, referring to flowchart 100, at step 102 a user may identify inclusion or exclusion criteria for use in reviewing the plurality of data sets, data input files, or other data sources. At step 104, a user may identify criteria for looping or reevaluation of data based on the one or more criteria identified at step 102, or based on additional criteria for determining how many looping iterations to undertake.

At step 106, the user may identify criteria or logic to validate the data that is brought into the aggregate. In some cases the validation criteria may be included with the inclusion/exclusion criteria data at step 102 and the looping criteria at step 104, however, in other cases it may stand on its own. For example, the final aggregate may be validated by resolution and validation engine 18 to ensure there is a monetary figure associated with the aggregate data record, to ensure that the aggregate records actually contain data, or based on any other validation review parameter contemplated in the art. At step 108 the data grouping platform builds the aggregate records, and at step 109, the data grouping platform is given information to build the aggregate cross-reference output links, as discussed in more detail below.

Figure 5:
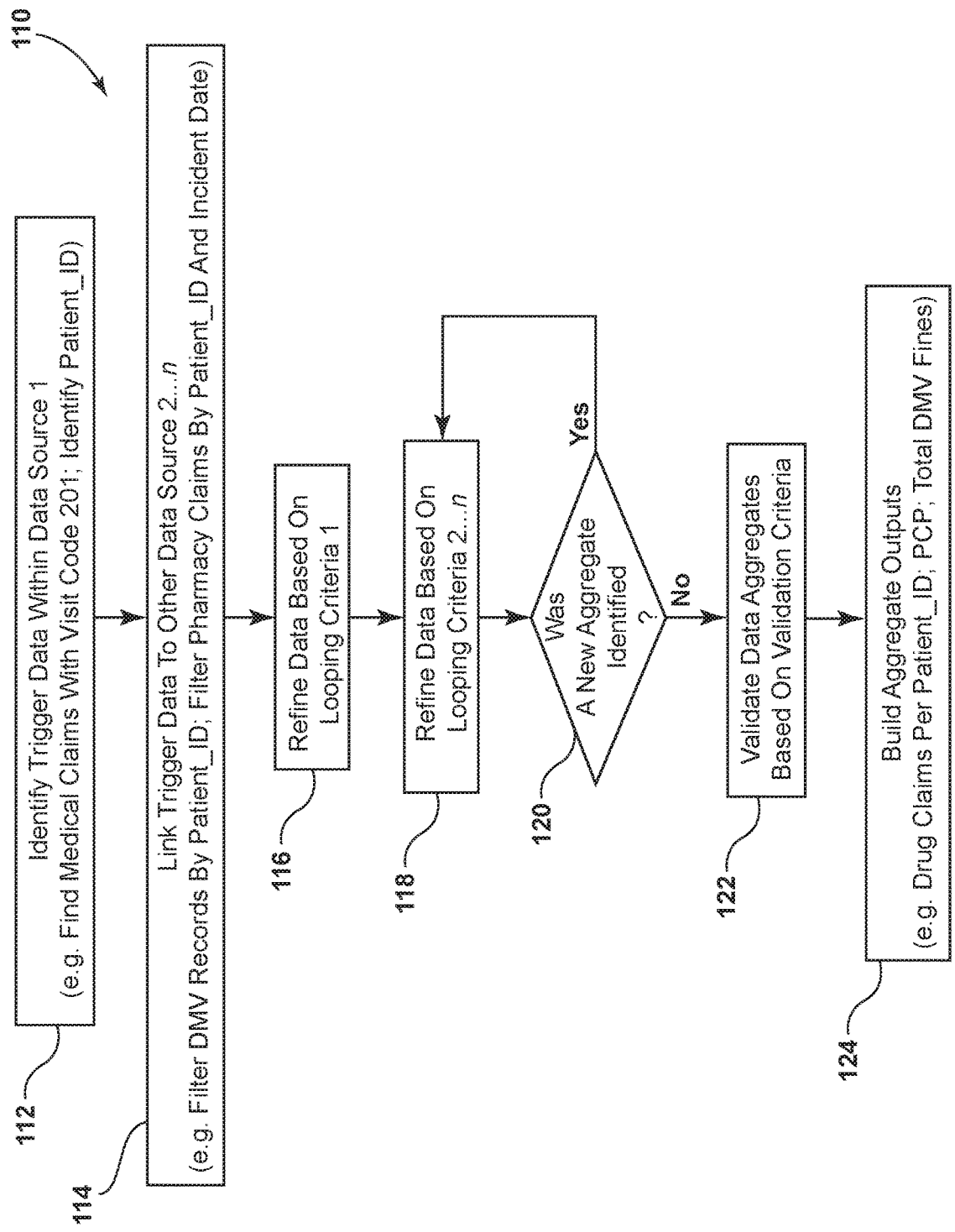
FIG. 5 also depicts a flowchart of a method related to building a data grouping platform, according to an embodiment of the present disclosure.

FIG. 5 provides a flowchart 110 describing exemplary processes of FIG. 4 in more detail, according to some aspects of the present disclosure. In some cases, the identification of inclusion and exclusion criteria within one or more data sources includes the identification of the trigger event or trigger data within all of the data sources identified by a user building the data grouping platform. In other cases the identification of how to include data consists of identifying trigger data within a first data set, and then linking data contained within the first data set to data in other data sets that may be relevant to the aggregate. In the illustrated embodiment depicted in flowchart 110, at step 112, the process includes identifying trigger data within a first data source. Referring to the illustrated embodiment, for example, step 112 may include finding all medical claims having visit code "201," and identifying the medical claim patient ID (for example, medical claim patient ID field 64 in FIG. 3). At step 114, the trigger data identified at step 112 may then be used to find related data in all additional data sources (i.e., the second data source to the $n^{th}$ data source of a plurality of identified data sources). For example, referring back to FIG. 3, after the medical claim patient ID field 64 is identified in the medical claims data source 62, the same patient ID may be found in other data sources, potentially signifying related information. Specifically, DMV records data source 72 may be filtered to identify data records related to DMV records patient ID field 74, and filtering pharmacy claims data source 68 may be filtered to identify data records related to pharmacy claim patient ID field 70.

Referring back to FIG. 4 at step 104, looping criteria may next be identified. The looping criteria may provide a mechanism for a record incorporation engine 16 to evaluate the data sets identified in step 102 to ensure thorough vetting of the data for the aggregate build. In some cases, the looping criteria may include a plurality of parameters by which to evaluate the plurality of data sources until no new aggregates are being created, no new records are identified, or until a defined end point. For example, portions of flowchart 110 depict an example of looping criteria flow according to at least one embodiment described herein. Specifically at step 116, once a plurality of data records have been identified at steps 112 and 114, the data is reviewed based on a first looping criteria. At step 118, the looping continues, again refining data based on additional looping criteria, i.e. a second looping criteria through an $n^{th}$ looping criteria or other defined end point.

As described above, the looping criteria may be driven by a plurality of different parameters relevant to the particular field or aggregate to be built as defined by a user in logic creation engine 14. For example, in some cases the data may be evaluated to determine if the data is truly relevant to the aggregate, or if the data should be discarded. In other cases, the data may be evaluated to determine if a single data aggregate should be split into multiple aggregates. For example, in the traffic incident medical care grouping system 60 example described herein, looping criteria may identify more than one traffic incident for a specific patient ID on a certain date. In such a case, the multiple traffic incidents may be separated into multiple aggregates for the ultimate aggregate build and cross-reference data build. In still other cases, looping criteria may include hard-coded looping criteria such as a certain number of looping passes, identifying a certain number of criteria per looping pass, or having a specific end point defined such as the creation of a threshold number of aggregates. According to at least one embodiment, the looping may continue until, at step 120, record incorporation engine 16 determines that there are no new aggregates.

If no additional aggregates are identified at step 120, the process may move to step 122, where resolution and validation engine 18 may validate the aggregates based on validation criteria provided by the user. Validation criteria may also be assigned by the user according to various parameters related to the aggregate. The validation phase includes an additional pass of the defined aggregate data to ensure that each aggregate should be retained. In some cases, the validation criteria may comprise identification of an incomplete aggregate record or an aggregate record with "junk" or non-existent data. For example, in the traffic incident medical care grouping system 60 embodiment exemplified herein, validation criteria may be defined to discard aggregates having no costs or dollar amount associated with the aggregate. In other cases, however, validation criteria may be based on other types of parameters on whether the aggregate has enough information to provide meaningful analysis and/or whether the aggregate should be separated into two or more aggregates for better analysis.

After validation at step 122, the data grouping platform builds aggregate outputs (e.g., data aggregates 24 in FIG. 1) at step 124 based on output criteria defined by a user. The output criteria may include a variety of parameters such as format for reporting the aggregate, fields to be included in the aggregate, and the like. Referring back to the traffic incident medical care grouping system 60 in FIG. 3, for example, the aggregate output itself may include an assigned aggregate ID field 80, an aggregate patient ID field 82, an aggregate number of drugs field 84, indicating the number drugs administered per patient ID, an assigned aggregate primary care physician (PCP) field 86, and an aggregate total fine field 88.

The aggregate build and outputs may also include identification of a number of aggregate cross-reference reports to separate the aggregate into specific component parts for analysis. Cross-reference tables may be built for any parameters related to the aggregate, as would be contemplated by a user when building the data grouping platform. For example, referring again to the traffic incident medical care grouping system 60 example in FIG. 3, an aggregate cross-reference table may include the aggregate medical claims link table 90, linking the aggregate patient ID field 82 to the aggregate record ID field 96. Other aggregate cross-reference tables may include the aggregate pharmacy claims link table 92, linking the aggregate patient ID field 82 to a pharmacy claims record ID field 97, and the aggregate DMV records link table 94, linking the aggregate patient ID field 82 to a DMV record ID 98.

Aspects of the present disclosure may further include provisions to build out and present a user interface and/or data entry mechanism for a user to identify the parameters for building out a data grouping platform to a data processing engine 12. In some cases this may comprise a data grouping platform code template (which may be based on the use of code schemas contemplated in the art) that may be automatically populated based on a user's identification of the parameters. In other cases this may include the build out of a data grouping platform build mechanism within one or more style sheet type code languages for grouping data. In at least one case, aspects of the present disclosure may provide a user interface for receiving user-defined parameters for building a data grouping platform, which may then be transcribed to any contemplated schema for execution by data processing engine 12.

Figure 6:
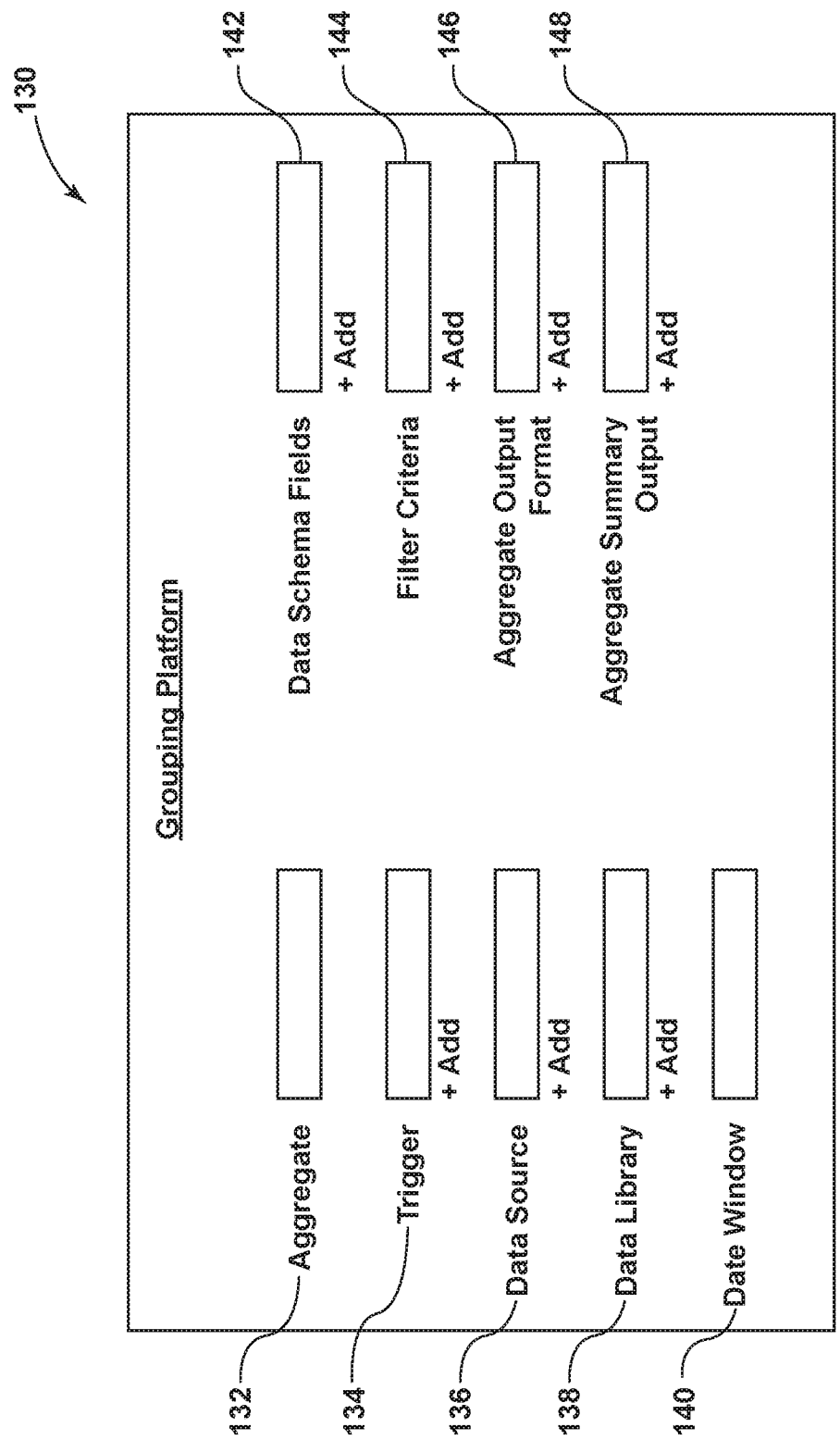
FIG. 6 depicts a user interface, according to an embodiment of the present disclosure.

FIG. 6 depicts an exemplary user interface 130, according to an embodiment described herein. As shown in FIG. 6, user interface 130 may include a plurality of data entry fields for identification and receipt of user-defined parameters. For example, a user may use an interface such as user interface 130 to identify an aggregate 132 to be built, as well as the trigger event(s) 134 to be used as a start of the aggregate 132. User interface 130 may also include entry fields for the identification of data sources 136 and data input libraries 138. As described above, data source(s) 136 may include any number of disparate data sources from which the data grouping platform may use to build the aggregate 132. Data input library(ies) 138 may include any type of additional data information, grouping parameters, or predefined lookup tables for building aggregate 132. For example, in a healthcare context, data input library(ies) 138 may include disease categorization or disease staging lookup tables that may be applicable to building an aggregate related to a medical event.

User interface 130 may further include a date or time window 140 for specification of a time period for which the aggregate records should be identified. Data grouping user interface 130 may include an input for one or more data schema fields 142, to identify one or more data schemes for creating the data aggregate or creating the logic surrounding the data aggregate. User interface 130 may also include an input area for filter criteria 144, which may include one or more mechanisms, such as a drop-down menu or other known means, for defining the logic and validation used within a user-defined data grouping platform. User interface 130 may also include an aggregate output format entry 146 and an aggregate cross-reference output entry 148 for a user to specify how to format the output for both the aggregate data and the aggregate cross-reference data.

Figure 7:
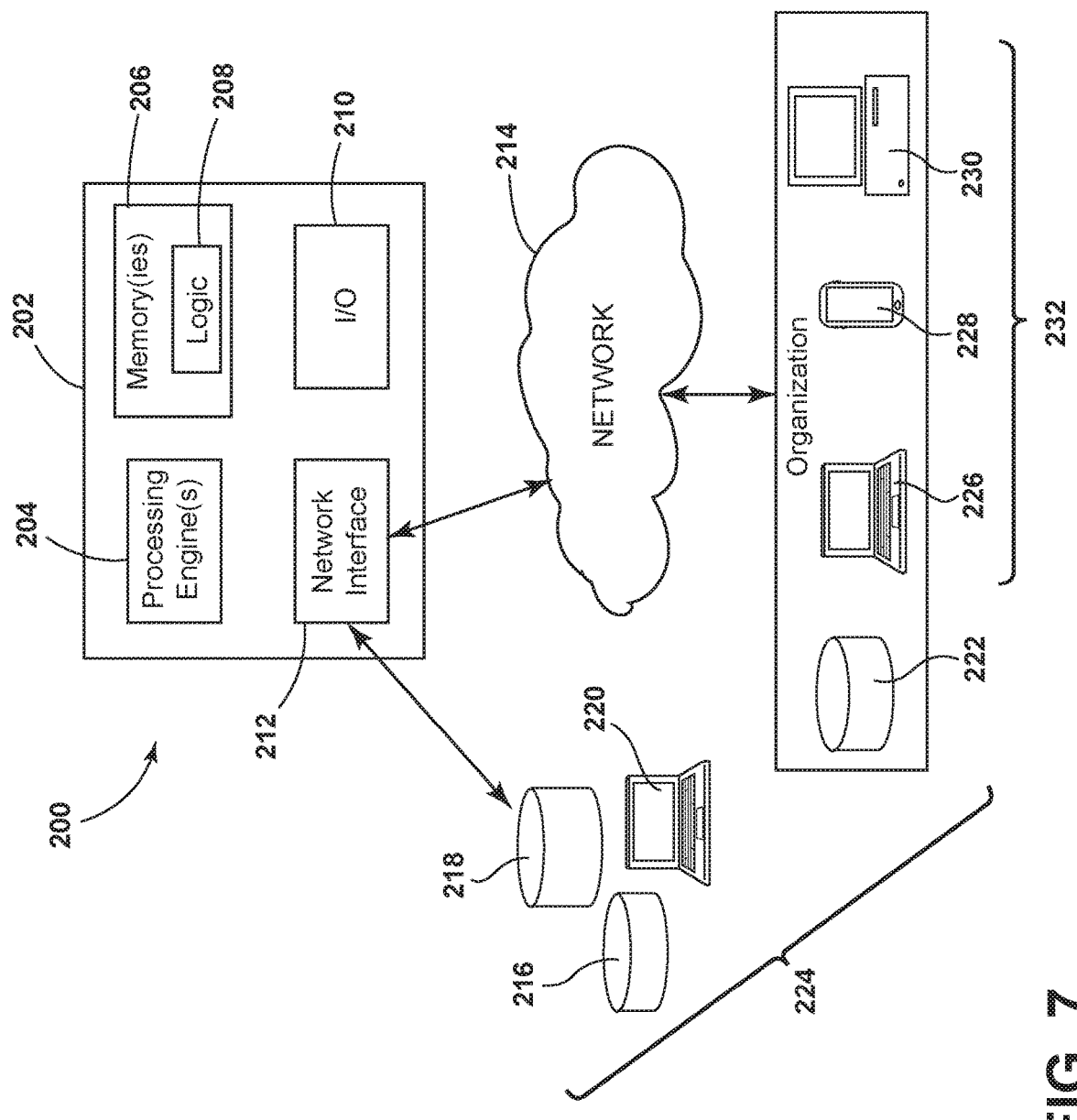
FIG. 7 depicts an exemplary schematic representation of a network environment in which aspects of the present disclosure may be implemented.

Embodiments of the methods and system described herein may utilize various computer software and hardware components, including but not limited to, servers, mainframes, desktops computers, databases, computer readable media, input/output devices, networking components and other components as would be known and understood by a person skilled in the art. FIG. 7 illustrates a networked operating environment 200 in which aspects of the present disclosure may be implemented, according to embodiments described herein. It should be understood, however, that operating environment 200 is only one example of a suitable environment for implementing methods described herein and is not intended to suggest any limitation as to the scope or functionality of the present disclosure. As depicted, operating environment 200 may include one or more servers 202, one or more databases 216, 218, 220 and 222, collectively, databases 224, and one or more access devices, such as computer/laptop computer 226, handheld device 228, and enterprise device 230, collectively access devices 232. Components of operating environment 200 may also be communicatively connected to one or more networks, such as network 214, for communication between the components.

Server 202 is generally representative of one or more servers suitable for serving data in the form of webpages or other markup language forms with associated applets, ActiveX controls, remote-invocation objects, or other related software and data structures, to service clients of various "thicknesses," and for processing multiples types of data sources. Server 202 may be configured as would be known by a skilled artisan and may include one or more processing engines 204, memory 206, one or more network interfaces 212, and/or one or more input/output devices 210 (such as a keyboard, mouse, display, etc.). Memory 206 may include a logic module 208 for creating and processing data grouping methodologies. In some embodiments, processing engine 204 may include one or more local or distributed processors, controllers, or virtual machines. As described above in relation to FIG. 1, processing engines 204 may include multiple processing engines, such as logic creation engine 14, data record incorporation engine 16, aggregate resolution and validation engine 18, and data enhancement engine 20.

Processing engine 204 may be configured in any convenient or desirable form as would be contemplated by a skilled artisan. Memory 206 may comprise one or more electronic, magnetic, or optical data-storage devices, and may include different types of memory. Memory 206 may store instructions, such as for logic module 208, for processing by processing engine 204. As described above in relation to FIG. 1, logic module 208 may include multiple logic modules such as any of logic creation engine 14, data record incorporation engine 16, aggregate resolution and validation engine 18, and data enhancement engine 20. Logic module 208 may include machine readable and/or executable instruction sets for performing and/or facilitating performance of methods and rendering graphical or tabular user interfaces as further described herein, including sharing one or more portions of this functionality in a client-server architecture, over a wireless or wireline communications network 214 with one or more access devices 232. The logic may be embodied in a variety of known software systems, including but not limited to, Analytic Definition Markup Language (ADML®); XML®, or other stylesheet language; Python®; and R®.

Databases 224 may include one or more electronic, magnetic, optical data-storage devices, or other data-storage devices which can include or are otherwise associated with respective indices (not shown). In some embodiments, databases 224 include medical, drug, and lab-related medical claims data. In other embodiments, databases 224 include and/or extract healthcare administrative data, such as medical claims and encounter data, from health plan, employer and government databases. In still other cases, databases 224 include non-medical related data, such as DMV-related data, as described above. In some embodiments, databases 224 additionally include guideline data sources, such as government and/or other public sources, government regulations and proprietary databases. According to aspects described herein, databases 224 may be connected to server 202 via network 214.

Server 202 may be accessed by one or more access devices, including, but not limited to personal computers, enterprise workstations, handheld devices, mobile telephones, or any other device capable of providing an effective user interface with a server or database. As depicted, in an embodiment of the disclosure, server 202 is connected to one or more access devices 232 via network 214. Network 214 may be any type of wireless or wireline data communications network contemplated by a skilled artisan, including, but not limited to a LAN, WAN, public-switched, satellite, or any other type of network as would be contemplated by a skilled artisan.

Accordingly, the present invention may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for building a data grouping platform, wherein the data grouping platform groups data from a plurality of data sets around a user-defined aggregate, the method comprising:
   receiving, by a processor, a format for the user-defined aggregate;
   receiving, by the processor, a user-defined event trigger, wherein the user-defined event trigger forms a basis for grouping data from the plurality of data sets around the user-defined aggregate;
   receiving, by the processor, criteria for grouping data from the plurality of data sets into the user-defined aggregate; and
   creating, by the processor, and storing in a computer readable, non-transient storage medium, instructions for performing a process to:
      responsive to identifying a first event meeting the user-defined trigger, identify a first set of data in the plurality of data sets using an identifier of an individual associated with the first event;
      review the first set of data from the plurality of data sets based on the criteria for grouping data from the plurality of data sets to identify a second set of data;
      determine that the second set of data includes a first portion associated with the identifier and the first event and a second portion associated with the identifier and a second event different than the first event and
      build a first aggregate comprising the first portion of the second set of data and a second aggregate comprising the second portion of the second set of data, based on the format for the user-defined aggregate.

2. The method of claim 1, wherein creating, by the processor, and storing in a computer readable, non-transient storage medium, further comprises a process to:
   identify first aggregate identifier for the first aggregate and a second aggregate identifier for the second aggregate.

3. The method of claim 2, wherein creating, by the processor, and storing in a computer readable, non-transient storage medium, further comprises a process to:
   link the first portion of the second set of data with the first aggregate identifier; and
   link the second portion of the second set of data with the second aggregate identifier.

4. The method of claim 1, wherein receiving, by the processor, criteria for grouping data from the plurality of data sets into the user-defined aggregate comprises:
   receiving criteria for identifying a data field in each of the plurality of data sets that is related to the user-defined aggregate.

5. The method of claim 1, wherein receiving, by the processor, criteria for grouping data from the plurality of data sets into the user-defined aggregate comprises:
   receiving criteria for identifying whether a date associated with each of the plurality of data sets is within a specified time window that is related to the user-defined aggregate.

6. The method of claim 1, wherein the criteria for grouping data from the plurality of data sets into a user-defined aggregate comprises a plurality of rules, and wherein creating, by the processor, and storing in a computer readable, non-transient storage medium, further comprises a process to:
   review the first set of data from the plurality of data sets multiple times to consider each rule in the plurality of rules, for grouping data from the plurality of data sets to identify the second set of data.

7. The method of claim 1, wherein the criteria for grouping data from the plurality of data sets into a user-defined aggregate comprises validation criteria, and wherein creating, by the processor, and storing in a computer readable, non-transient storage medium, further comprises a process to:
   review the second set of data based on the validation criteria to identify a validated set of data within the second set of data; and
   build the first aggregate comprising the validated set of data within the second set of data.

8. The method of claim 7, wherein the validation criteria comprises determining whether the second set of data should be discarded.

9. The method of claim 7, wherein the validation criteria comprises determining whether the second set of data should be merged with an existing aggregate.

10. The method of claim 7, wherein creating, by the processor, and storing in a computer readable, non-transient storage medium, further comprises a process to:
    create cross-reference data that summarizes the first aggregate and the second aggregate.

11. The method of claim 1, wherein the first-aggregate and the second aggregate are related to healthcare events.

12. A system for building a data grouping platform around a user-defined aggregate comprising:
    a user interface for receiving the user-defined aggregate, a user-defined event trigger, and criteria for grouping data from a plurality of data sets;
    a data processing engine configured to:
       receive, a format for the user-defined aggregate;

receive the user-defined event trigger, wherein the user-defined event trigger forms a basis for grouping data from a plurality of data sets around the user-defined aggregate;

receive the criteria for grouping data from the plurality of data sets into the user-defined aggregate; and create and store, in a computer readable, non-transient storage medium, instructions for performing a process to:

responsive to identifying a first event meeting the user-defined trigger, identify a first set of data from the plurality of data sets using an identifier of an individual associated with the first event;

review the first set of data from the plurality of data sets based on the criteria for grouping data from the plurality of data sets to identify a second set of data;

determine that the second set of data includes a first portion associated with the identifier and the first event and a second portion associated with the identifier and a second event different than the first event and build a first aggregate comprising the first portion of the second set of data and a second aggregate comprising the second portion of the second set of data, based on the format for the user-defined aggregate.

13. The system of claim 12, wherein the criteria for grouping data from the plurality of data sets comprises grouping data by a time window.

14. The system of claim 12, wherein the criteria for grouping data from the plurality of data sets comprises grouping data by a field within the data.

15. The system of claim 12, wherein the criteria for grouping data from the plurality of data sets comprises excluding data based on a field within the data.

16. The system of claim 12, wherein the criteria for grouping data from the plurality of data sets comprises a first criteria, and wherein the data processing engine is further configured to create and store, in a computer readable, non-transient storage medium, a process to:

review the first set of data from the plurality of data sets based on the first criteria and a second criteria for grouping data from the plurality of data sets to identify the second set of data.

17. The system of claim 12, wherein the criteria for grouping data from the plurality of data sets into a user-defined aggregate comprises validation criteria, and wherein the data processing engine is further configured to create and store, in a computer readable, non-transient storage medium, a process to:

review the second set of data based on the validation criteria to identify a validated set of data within the second set of data; and build the first aggregate and the second aggregate comprising the validated set of data within the second set of data.

18. A computer program product for building a data grouping platform, the computer program product comprising a computer readable, non-transient storage medium having program instructions embodied therewith, the program instructions executable by a data processing engine to cause the data processing engine to:

receive a format for the user-defined aggregate;

receive a user-defined event trigger, wherein the user-defined event trigger forms a basis for grouping data from the plurality of data sets around the user-defined aggregate;

receive a plurality of criteria for grouping data from the plurality of data sets into the user-defined aggregate; and create and store in a computer readable, non-transient storage medium, instructions for performing a process to:

responsive to identifying a first event meeting the user-defined event trigger, identify a first set of data in the plurality of data sets using an identifier of an individual associated with the first event;

review the first set of data from the plurality of data sets based on a first criteria of the plurality of criteria for grouping data from the plurality of data sets, to identify a second set of data;

review the second set of data based on a validation criteria of the plurality of criteria for grouping data from the plurality of data sets, to identify a validated set of data;

determine that the validated set of data includes a first portion associated with the identifier and the first event and a second portion associated with the identifier and a second event different than the first event and build a first aggregate comprising the first portion of the validated set of data and a second aggregate comprising the second portion of the validated set of data, based on the format for the user-defined aggregate.

19. The computer program product for building a data grouping platform of claim 18, wherein:

the first criteria comprises a specific time window; and reviewing the second set of data based on the validation criteria comprises identifying the first aggregate and the second aggregate within the time window.

20. The computer program product for building a data grouping platform of claim 18, wherein:

the criteria for grouping data from the plurality of data sets into a user-defined aggregate comprises a plurality of rules, and reviewing the second set of data comprises reviewing the first set of data from the plurality of data sets multiple times to consider each rule in the plurality of rules for grouping data from the plurality of data sets to identify the second set of data.

* * * * *